(12) United States Patent
Gong (10) Patent No.: US 7,857,541 B2
(45) Date of Patent: Dec. 28, 2010

(54) CONNECTING/DISCONNECTING MECHANISM AND COMPOSITE APPARATUS

(75) Inventor: Guangzhao Gong, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 508 days.

(21) Appl. No.: 11/862,724

(22) Filed: Sep. 27, 2007

(65) Prior Publication Data
US 2008/0078071 A1    Apr. 3, 2008

(30) Foreign Application Priority Data
Sep. 30, 2006    (CN)    ......................... 2006 1 0144741

(51) Int. Cl.
*H01R 13/627* (2006.01)
(52) U.S. Cl. ................... 403/322.3; 710/303; 600/437; 361/686
(58) Field of Classification Search ............. 403/322.3, 403/322.4, 325; 710/303; 361/686; 439/351, 439/353, 929; 600/437
See application file for complete search history.

(56) References Cited

U.S. PATENT DOCUMENTS

| | | | | |
|---|---|---|---|---|
| 4,902,156 | A | * | 2/1990 | Deisler et al. ................. 403/24 |
| 4,959,609 | A | | 9/1990 | Prokopp et al. |
| 5,580,182 | A | * | 12/1996 | Lin ............................ 403/325 |
| 5,870,283 | A | * | 2/1999 | Maeda et al. .......... 361/679.44 |
| 5,926,627 | A | * | 7/1999 | Sugimura ................... 710/303 |
| 5,997,323 | A | * | 12/1999 | Youn .......................... 439/159 |
| 6,034,869 | A | * | 3/2000 | Lin ........................ 361/679.43 |
| 6,061,233 | A | * | 5/2000 | Jung ...................... 361/679.41 |
| 6,061,234 | A | * | 5/2000 | Broder et al. ......... 361/679.41 |
| 6,069,790 | A | * | 5/2000 | Howell et al. ......... 361/679.43 |
| 6,093,039 | A | * | 7/2000 | Lord ........................... 439/155 |
| 6,113,409 | A | | 9/2000 | Park |
| 6,119,184 | A | * | 9/2000 | Takahama ................... 710/303 |
| 6,216,195 | B1 | * | 4/2001 | Lee et al. ..................... 710/303 |
| 6,217,339 | B1 | | 4/2001 | Tsubata |
| 6,226,053 | B1 | | 5/2001 | Cho |
| 6,275,378 | B1 | * | 8/2001 | Lee et al. .............. 361/679.55 |

(Continued)

FOREIGN PATENT DOCUMENTS

JP    2006-037511    2/2006

*Primary Examiner*—Joshua T Kennedy
(74) *Attorney, Agent, or Firm*—Armstrong Teasdale LLP (57) ABSTRACT

A connecting/disconnecting mechanism able to connect and disconnect two units easily, as well as a composite apparatus having such a connecting/disconnecting mechanism, can be provided. A hook portion has a hook, the hook having a branch at a longitudinal front end thereof, the branch having a front-end side face inclined downward toward the front end, with resilient force being applied in the direction of the branch, the hook being moved in the front end direction with an external force applied thereto and returning to its original position upon extinction of the external force, the hook being adapted to reciprocate with respect to the front end direction in a state in which the front end portion is displaced in the direction opposite to the branch to a greater extent than the length of the branch, and a hook receptacle portion has an abutting member adapted to be pushed by the front end of the hook and move when the hook moves in the front end direction and a hook receptacle adapted to engage the branch prior to movement of the hook in the front end direction and move together with the abutting member in a disengaged state from the branch when the hook moves in the front end direction.

15 Claims, 11 Drawing Sheets

U.S. PATENT DOCUMENTS

| | | | |
|---|---|---|---|
| 6,366,458 B1* | 4/2002 | Yoshida et al. | 361/679.41 |
| 6,411,537 B2* | 6/2002 | Helot | 361/679.41 |
| 6,424,524 B2* | 7/2002 | Bovio et al. | 361/679.45 |
| 6,687,123 B2* | 2/2004 | Kitahara | 361/695 |
| 6,741,462 B2* | 5/2004 | Kamphuis et al. | 361/679.02 |
| 6,954,981 B2 | 10/2005 | Suzuki | |
| 7,085,132 B2* | 8/2006 | Schlesener et al. | 361/679.23 |
| 7,139,168 B2* | 11/2006 | DeLuga et al. | 361/679.58 |
| 7,142,421 B2* | 11/2006 | Cheng et al. | 361/679.57 |
| 7,256,990 B2* | 8/2007 | Grunow et al. | 361/679.41 |
| 7,286,344 B2* | 10/2007 | Kim | 361/679.41 |
| 7,405,929 B1* | 7/2008 | Chuang et al. | 361/679.41 |
| 7,591,786 B2* | 9/2009 | Holmberg et al. | 600/437 |
| 7,633,750 B2* | 12/2009 | Fan et al. | 361/679.43 |
| 2003/0147209 A1* | 8/2003 | Oross et al. | 361/686 |
| 2003/0231465 A1* | 12/2003 | Weng | 361/686 |
| 2004/0012922 A1* | 1/2004 | Kamphuis et al. | 361/686 |
| 2004/0075980 A1* | 4/2004 | Park | 361/686 |
| 2004/0150963 A1* | 8/2004 | Holmberg et al. | 361/741 |
| 2005/0047104 A1* | 3/2005 | Grunow et al. | 361/801 |
| 2006/0061961 A1* | 3/2006 | Yin et al. | 361/686 |
| 2006/0139875 A1* | 6/2006 | Cheng et al. | 361/686 |
| 2007/0177347 A1* | 8/2007 | Nishiyama | 361/686 |
| 2008/0100995 A1* | 5/2008 | Ryder et al. | 361/679 |

* cited by examiner

CONNECTING/DISCONNECTING MECHANISM AND COMPOSITE APPARATUS

CROSS REFERENCE TO RELATED APPLICATIONS

This application claims the benefit of Chinese Patent Application No. 200610144741.2 filed Sep. 30, 2006

BACKGROUND OF THE INVENTION

The present invention relates to a connecting/disconnecting mechanism and more particularly a connecting/disconnecting mechanism having a hook portion and a hook receptacle portion provided in one and the other, respectively, of two connectable and disconnectable units, as well as a composite apparatus provided with the connecting/disconnecting mechanism.

A connecting/disconnecting mechanism is used for making two unit connectable and disconnectable mechanically. The connecting/disconnecting mechanism comprises a hook portion and a hook receptacle portion provided in one and the other, respectively, of two units. The two units are connected by engagement of the hook portion and the hook receptacle portion and are disconnected by disengagement of both portions (see, for example, Patent Literature 1).

[Patent Literature 1] Japanese Patent Laid-Open Publication No. 2006-037511.

Connecting/disconnecting mechanisms of various constructions are known, depending on the type of an object of application. For example, in the case where one of two units is a portable ultrasonic diagnosing device and the other is a docking station provided with an electronic circuit for the extension of function and wheels for travel, it is necessary that the two should be connected and disconnected easily.

SUMMARY OF THE INVENTION

Therefore, it is an object of the invention to provide a connecting/disconnecting mechanism capable of connecting and disconnecting two units easily, as well as a composite apparatus provided with the connecting/disconnecting mechanism.

In one aspect of the invention there is provided a connecting/disconnecting mechanism having a hook portion and a hook receptacle portion provided in one and the other, respectively, of two connectable and disconnectable units, the hook portion having a hook formed with a branch at a longitudinal front end thereof, the branch having a front-end side face inclined downward toward the front end, with resilient force being applied in the direction of the branch, the hook being moved in the front end direction with an external force applied thereto and returning to its original position upon extinction of the external force, the hook being adapted to reciprocate with respect to the front end direction in a state in which the front end portion is displaced in the direction opposite to the branch to a greater extent than the length of the branch, the hook receptacle portion having: an abutting member adapted to be pushed by the front end of the hook and move when the hook moves in the front end direction; and a hook receptacle adapted to engage the branch prior to movement of the hook in the front end direction, and adapted to move together with the abutting member in a disengaged state from the branch when the hook moves in the front end direction.

In another aspect of the invention there is provided a composite apparatus comprising two connectable and disconnectable units, the two units having a hook portion and a hook receptacle portion, respectively, the hook portion having a hook formed with a branch at a longitudinal front end thereof, the branch having a front-end side face inclined downward toward the front end, with resilient force being applied in the direction of the branch, the hook being moved in the front end direction with an external force applied thereto and returning to its original position upon extinction of the external force, the hook being adapted to reciprocate with respect to the front end direction in a state in which the front end portion is displaced in the direction opposite to the branch to a greater extent than the length of the branch, the hook receptacle portion having: an abutting member adapted to be pushed by the front end of the hook and move when the hook moves in the front end direction; and a hook receptacle adapted to engage the branch prior to movement of the hook in the front end direction, and adapted to move together with the abutting member in a disengaged state from the branch when the hook moves in the front end direction.

For facilitating the disconnecting operation it is preferable for the hook portion to have a handle for applying an external force to the hook.

For enhancing the connection strength it is preferable for the hook portion to have the plural hooks and for the hook receptacle portion to have the plural abutting members and the plural hook receptacles correspondingly to the plural hooks.

For further enhancing the connection strength it is preferable for the hook portion to have a second hook whose position is fixed and for the hook receptacle portion to have a second hook receptacle, the second hook receptacle being adapted to engage the second hook before the hook moves in the front end direction and being adapted to move together with the abutting member and become disengaged from the second hook when the hook moves in the front end direction.

For making an electrical connection it is preferable for one of the two units to have an electric connector plug whose position is fixed and for the other unit to have an electric connector receptacle adapted to engage the electric connector plug in a state in which the hook receptacle engages the branch of the hook.

For providing a composite apparatus able to travel it is preferable for one of the two units to be a support base having wheels for travel and for the other unit to be an electronic device capable of being mounted on the support base.

For facilitating positioning during connection it is preferable for the support base to have a guide rail on an upper surface thereof and for the electronic device to have a slider on a bottom thereof, the slider being engaged with the rail.

For providing a composite apparatus of a satisfactory function it is preferable for the support base to have an electronic circuit for the electronic device.

For enhancing the degree of freedom in using the electronic device it is preferable that the electronic device be capable of being removed from the support base and be portable.

To obtaining an ultrasonic diagnosing device of high degree of freedom in usage, it is preferable that the electronic device is the ultrasonic diagnosing device.

For providing an ultrasonic diagnosing device of a high degree of freedom in use it is preferable for the electronic device to be an ultrasonic diagnosing device.

The connecting/disconnecting mechanism according to the invention has a hook portion and a hook receptacle portion provided in one and the other, respectively, of two connectable and disconnectable units, the hook portion having a hook formed with a branch at a longitudinal front end thereof, the branch having a front-end side face inclined downward toward the front end, with resilient force being applied in the direction of the branch, the hook being moved in the front end direction with an external force applied thereto and returning to its original position upon extinction of the external force, the hook being adapted to reciprocate with respect to the front end direction in a state in which the front end portion is displaced in the direction opposite to the branch to a greater extent than the length of the branch, the hook receptacle portion having: an abutting member adapted to be pushed by the front end of the hook and move when the hook moves in the front end direction; and a hook receptacle adapted to engage the branch prior to movement of the hook in the front end direction, and adapted to move together with the abutting member in a disengaged state from the branch when the hook moves in the front end direction. Thus, it is possible to provide a connecting/disconnecting mechanism able to connect and disconnect two units easily, as well as a composite apparatus provided with such a connecting/disconnecting mechanism.

Further objects and advantages of the present invention will be apparent from the following description of the preferred embodiments of the invention as illustrated in the accompanying drawings.

BRIEF DESCRIPTION OF THE DRAWINGS

FIG. 7($a$) and FIG. 7($b$) illustrate a state of connection made by the hook.

FIG. 9($a$) and FIG. 9($b$) illustrate a disconnected state.

DETAILED DESCRIPTION OF THE INVENTION

Figure 1:
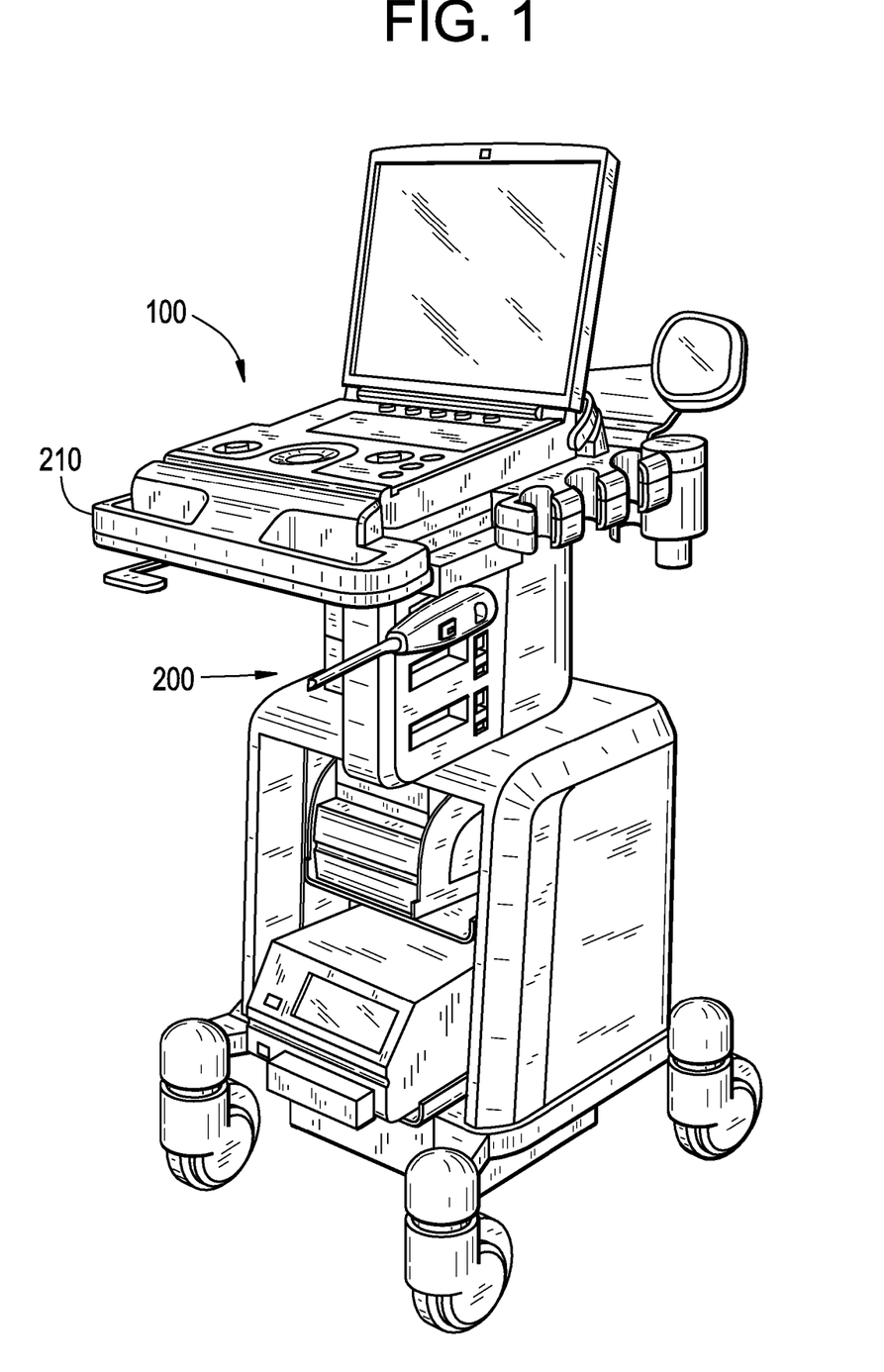
FIG. 1 illustrates the construction of an example of the best mode for carrying out the invention in terms of a halftone photograph.

The best mode for carrying out the invention will be described hereinunder with reference to the drawings. The invention is not limited to the best mode for carrying out the invention. FIG. 1 is an appearance diagram showing the construction of an ultrasonic diagnosing system related to the invention. This system is an example of the best mode for carrying out the invention. With the construction of this system there is shown an example of the best mode carrying out the invention with respect to the composite apparatus. Further, with part of the construction of this system there is shown an example of the best mode for carrying out the invention with respect to the connecting/disconnecting mechanism.

As shown in FIG. 1, this system is constituted by a combination of two units 100 and 200. One unit 100 is, for example, an ultrasonic diagnosing device having an outline similar to a notebook-size PC (personal computer). The other unit 200 is, for example, a docking station for the ultrasonic diagnosing device. The docking station is provided with an electronic circuit for the extension of function of the ultrasonic diagnosing device, a power supply circuit, and other accessories. The docking station has wheels for travel and functions also as a cart.

The unit 100 is not limited to the ultrasonic diagnosing device, but may be a suitable electronic or non-electronic device. The hint 200 is not limited to the docking station for the ultrasonic diagnosing device, but may be a support base for an electronic or non-electronic device. In this case, the wheels for travels are not always needed.

The following description is now provided about an example wherein the units 100 and 200 are an ultrasonic diagnosing device and a docking station for the same device, respectively. However, also in the case of a composite apparatus constituted by any other combination, there will be obtained the same function and effect.

The ultrasonic diagnosing device 100 is placed on a horizontal top board 210 of the docking station 200. In this state, both are connected mechanically using a connecting/disconnecting mechanism or connected electrically using a connector. As to the connecting/disconnecting mechanism, a description will be given later.

The ultrasonic diagnosing device 100, together with the docking station 200, constitutes a full-equipped ultrasonic diagnosing system. The ultrasonic diagnosing device 100 can be removed from the docking station 200 and can make a basic ultrasonic diagnosis as a single device.

Since the ultrasonic diagnosing device 100 has an outline similar to a notebook-size PC, it is convenient for use as a portable device.

Figure 2:
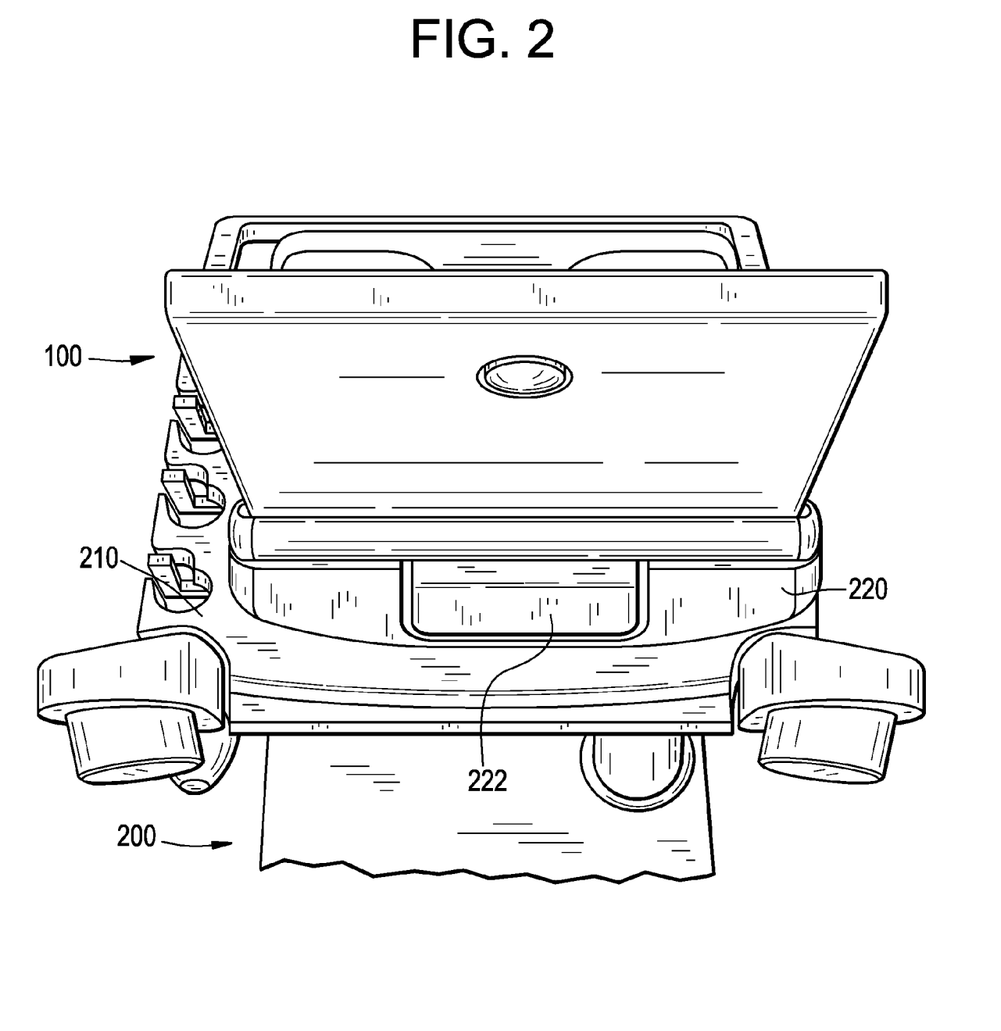
FIG. 2 illustrates the construction of an example of the best mode for carrying out the invention in terms of a halftone photograph from another viewpoint.

FIG. 2 shows a connected state of both ultrasonic diagnosing device 100 and docking station 200 as seen from behind. As shown in the same figure, a rear surface of the ultrasonic diagnosing device 100 is abutted from the front side against a bank 220 of the top board 210 and in this state both are connected together mechanically and electrically.

A handle 222 capable of being pushed in is provided in the bank 220. By pushing in the handle 222 forward, the mechanical and electrical connection between the ultrasonic diagnosing device 100 and the docking station 200 can be released.

Figure 3:
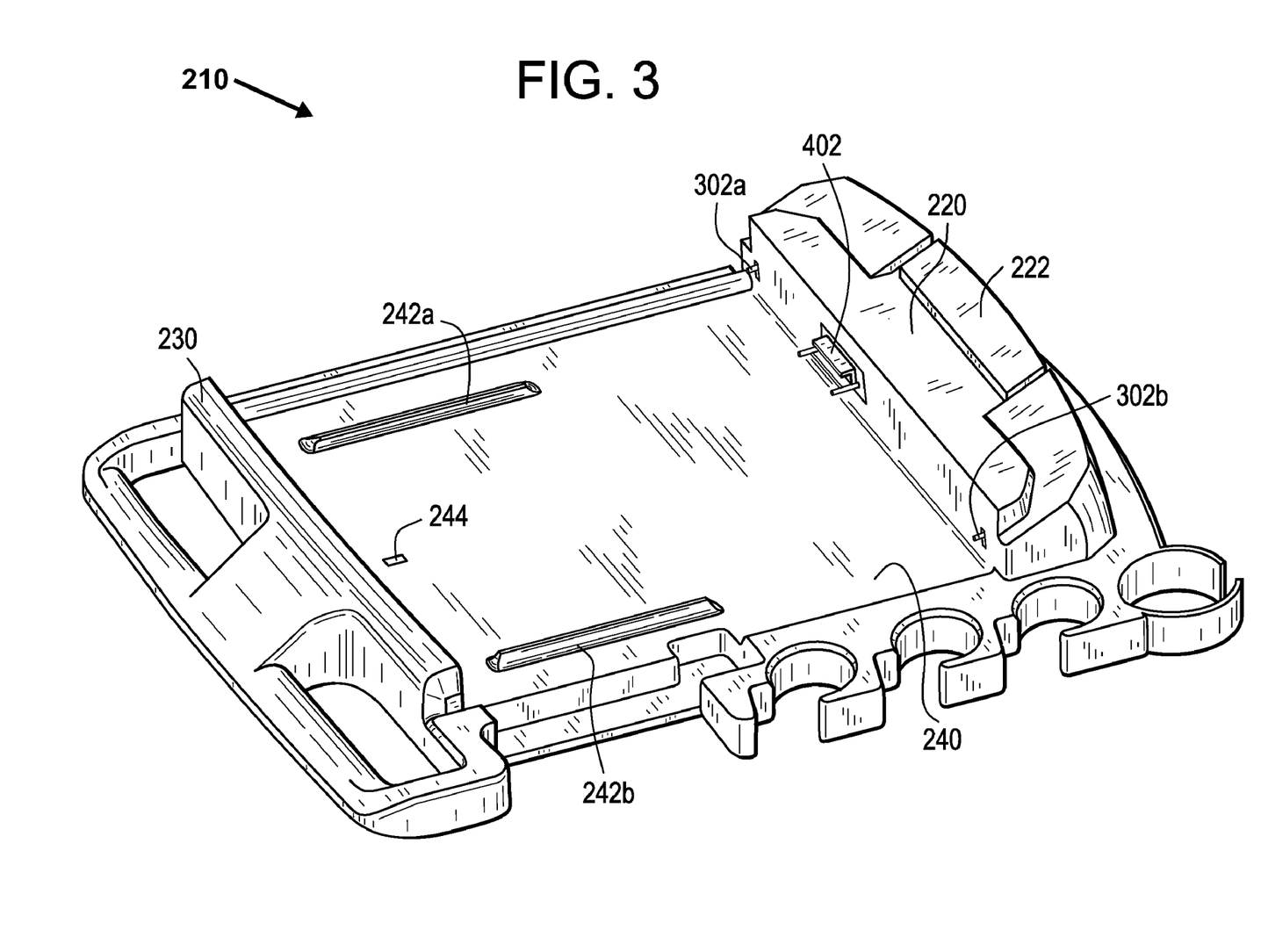
FIG. 3 illustrates the construction of a top board.

FIG. 3 shows the construction of the top board 210. As shown in the same figure, the top board 210 has two banks 220 and 230. The banks 220 and 230 are rear and front banks, respectively. A flat board 240 is disposed between the rear bank 220 and the front bank 230 and the ultrasonic diagnosing device 100 is placed on the flat board 240.

A pair of hooks 302$a$ and 302$b$ and a connector plug 402 are projected forward from a front wall of the rear bank 220. The hooks 302$a$, 302$b$ and the connector plug 402 correspond respectively to a pair of hook receptacles and a connector receptacle which are provided on the rear surface side of the ultrasonic diagnosing device 100.

A pair of rails 242$a$ and 242$b$ and a hook 244 are provided on the flat board 240. The rails 240$a$ and 240$b$ are laid in a direction perpendicular to the bank 220. The rails 242$a$, 242$b$ and the hook 244 correspond respectively to a pair of sliders and a hook receptacle which are provided on a bottom of the ultrasonic diagnosing device 100.

When the ultrasonic diagnosing device 100 is put on the flat board 240 in such a manner that its rear surface confronts a front surface of the bank 220 and is then pushed against the bank 220 with the rails 242$a$ and 242$b$ as guides, the hooks 302$a$, 302$b$, 244 and the connector plug 402 come into engagement with three corresponding hook receptacles and connector receptacle in the ultrasonic diagnosing device 100, whereby there is formed a mechanical and electrical connection between the ultrasonic diagnosing device 100 and the docking station 200.

Figure 4:
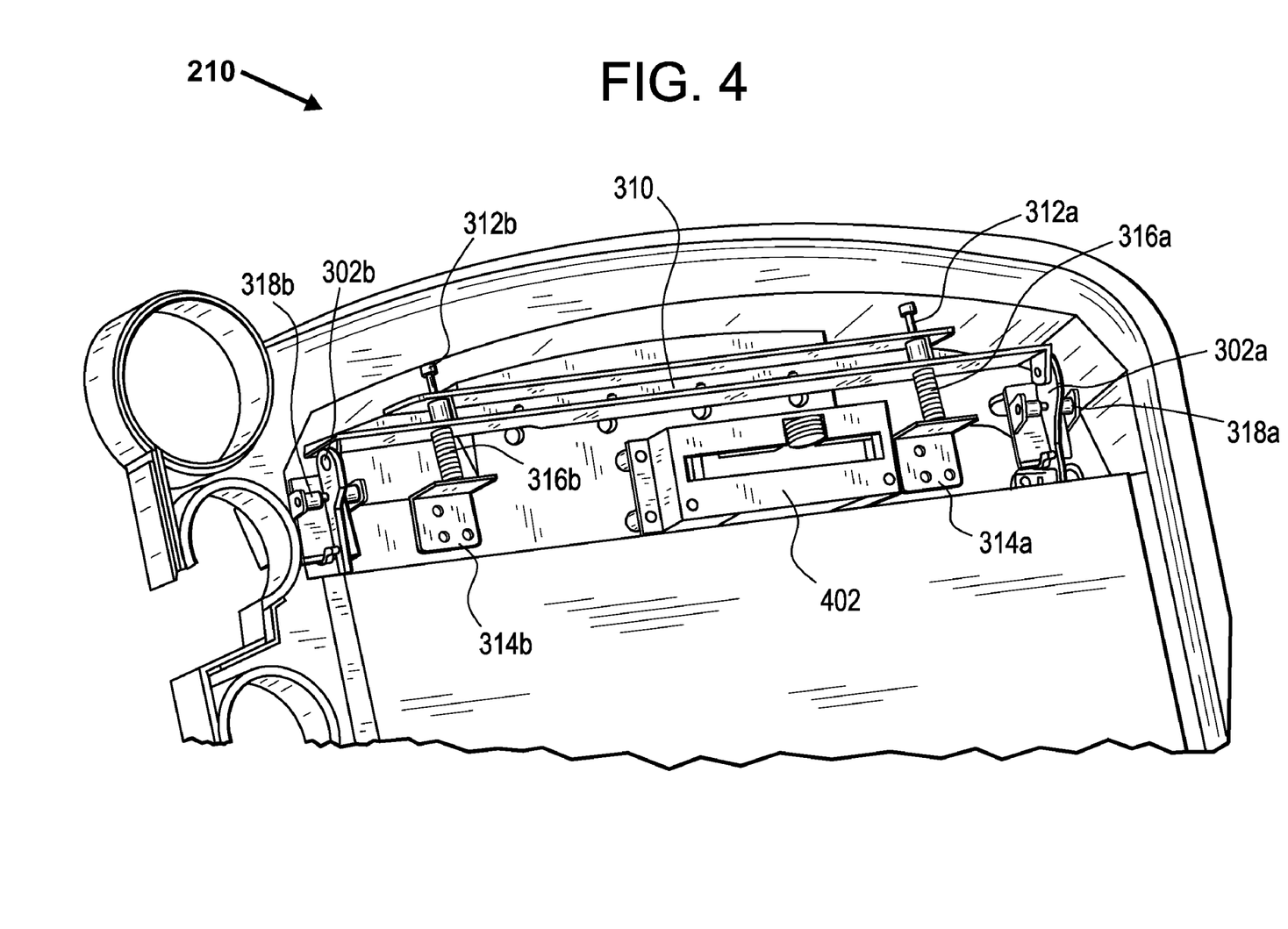
FIG. 4 illustrates the construction of a hook drive mechanism.

FIG. 4 shows the construction of a drive mechanism for the hooks 302a and 302b. FIG. 4 is a rear view of the top board 210. As shown in the same figure, the drive mechanism for the hooks 302a and 302b is installed in an internal space of the bank 220.

The drive mechanism for the hooks 302a and 302b has a bracket 310. The bracket 310, which has a U-shaped cross section, is loosely fitted on a pair of support shafts 312a and 312b and is thereby supported in parallel with the bank 220.

The support shafts 312a and 312b extend through the bracket 310 perpendicularly and one ends thereof are fixed to an inner wall of the bank 220, while opposite ends thereof are fixed to longitudinal plate portions of a pair of L-shaped plates 314a and 314b, respectively. Lateral plate portions of the L-shaped plates 314a and 314b are fixed to the ceiling of the bank 220.

Coiled springs 316a and 316b are mounted on the support shafts 312a and 312b at positions between the bracket 310 and the L-shaped plates 314a, 314b and their repulsive forces are exerted between the bracket 310 and the L-shaped plates 314a, 314b. With the repulsive forces, the bracket 310 is pushed constantly toward the inner part of the bank 220 and stops in abutment against a stopper. This position is a predetermined regular position of the bracket 310.

The bracket 310 is made integral with the handle 222 on the ceiling side. Consequently, when the handle 222 is pushed in forward by hand, the bracket 310 advances against the repulsive forces of the coiled springs 316a and 316b, while when the hand is released from the handle 222, the bracket 310 retreats with the repulsive forces of the coiled springs 316a, 316b and returns to its original position.

The hooks 302a and 302b are attached perpendicularly to both ends of the bracket 310. Mounting portions of the hooks 302a and 302b for mounting to the bracket 310 are formed by hinges and resilient force acting to rotate the hooks 302a and 302b in the direction of the ceiling is exerted on those hinges.

The hooks 302a and 302b are provided on the ceiling side with fixed pins 318a and 318b, respectively. The pins 318a and 318b inhibit rotation of the hooks 302a and 302b induced by the resilient force and restrict the attitude of the hooks 302a and 302b so that their longitudinal direction is substantially coincident with the direction in which the bracket 310 advances and retreats. In such an attitude-restricted state the hooks 302a and 302b advance and retreat together with the bracket 310.

Front end portions of the hooks 302a and 302b extend through a front wall of the bank 220 and project to the exterior. The amount of the projection becomes large when the hooks 302a and 302b move forward and becomes small when the hooks move backward. A front end portion of the connector plug 402 also extends through the front wall of the bank 220 and projects to the exterior.

Figure 5:
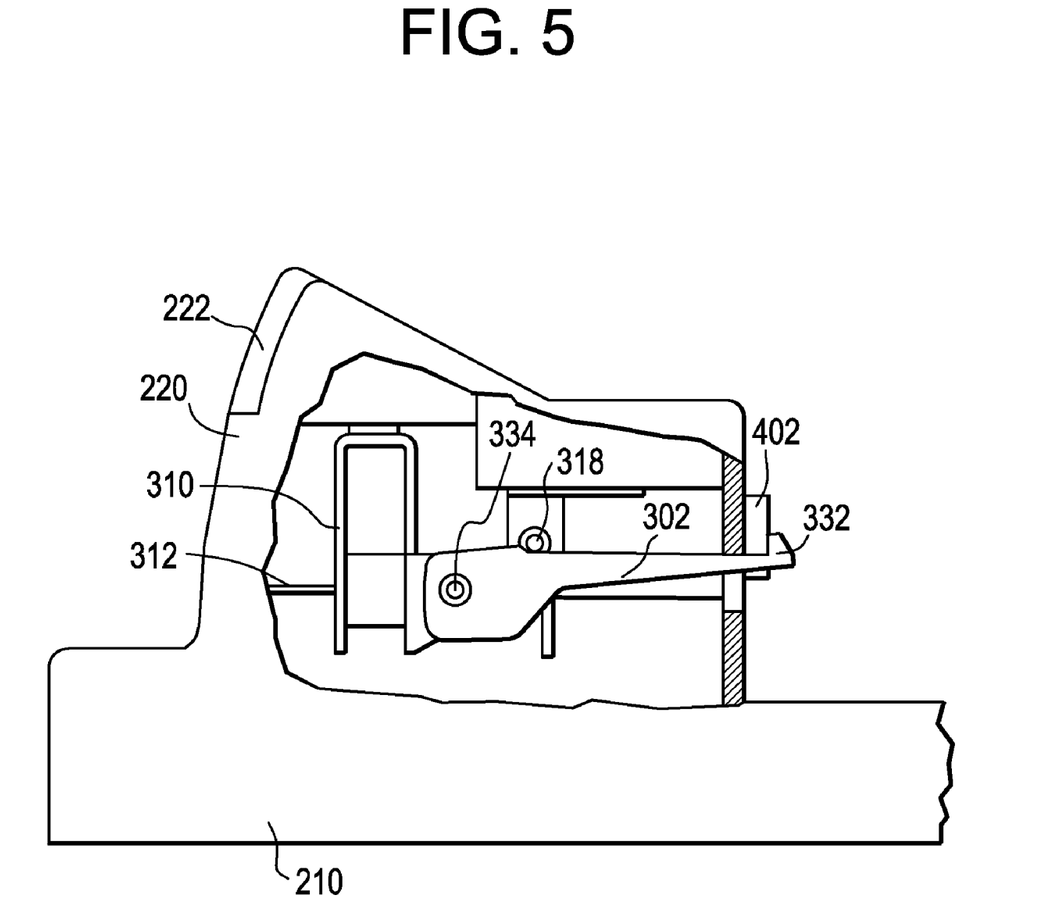
FIG. 5 illustrates the construction of a hook.

FIG. 5 is a side view of a drive mechanism for the hooks 302a and 302b. In FIG. 5, a hook 302 is a generic term for the hooks 302a and 302b, a pin 318 is a generic term for the pins 318a and 318b, and a support shaft 312 is a generic term for the support shafts 312a and 312b. This is also true in the following.

As shown in FIG. 5, the hook 302 has a branch 332 at a front end portion in its longitudinal direction. The direction of the branch 332 is the same as the direction of a rotating force acting on the hook 302. A side face of the branch 332 is inclined in such a manner that the front end side of the hook 302 declines toward the front end.

A stepped portion is formed at the portion of the hook 302 which portion is in contact with the pin 318. The stepped portion is high on its side close to the hinge 334 and low on its side distant from the hinge 334. With the handle 222 not in operation, i.e., at a predetermined regular position thereof, the stepped portion is in contact with the pin 318 at its low portion and the branch 332 lies on an extension of the low portion in the stepped portion.

Figure 6:
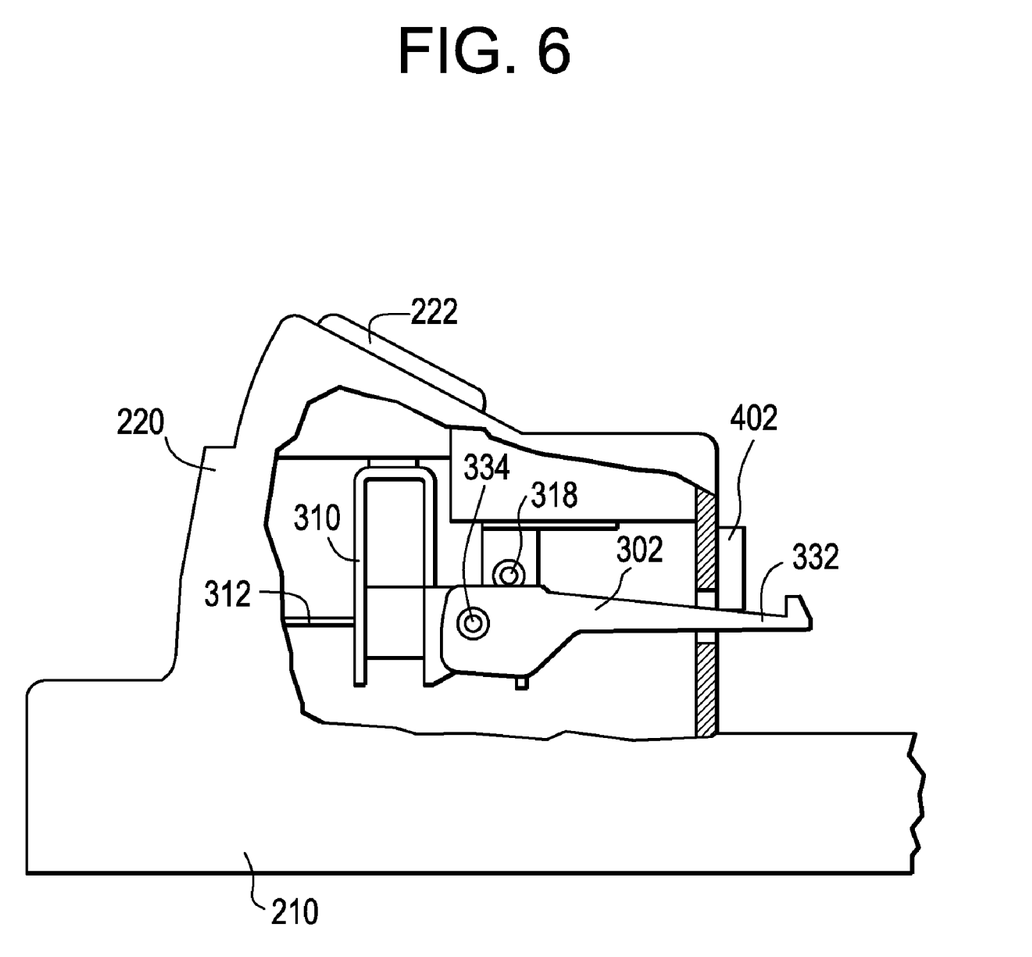
FIG. 6 illustrates a state of operation of the hook.

In this state, when the handle 222 is pushed forward, causing the hook 302 to move forward, the high portion in the stepped portion comes into contact with the pin 318, as shown in FIG. 6, whereby the front end portion of the hook 302 lowers. That is, the hook 302 having the stepped portion constitutes a cam mechanism together with the pin 318. The amount of lowering of the front end portion by the cam mechanism is larger than the length of the branch 332. The hook 302 moves forward in such a lowered state of the front end. The amount of the forward movement corresponds to the amount of depression of the handle 222.

When the hand is released from the handle 222, the hook 302 moves backward with resilient force. As a result, the hook 302 returns to its regular position, further, as shown in FIG. 5, the low portion in the stepped portion comes into contact with the pin 318 and the hook 302 stops in a raised state of its front end.

Figure 7A:
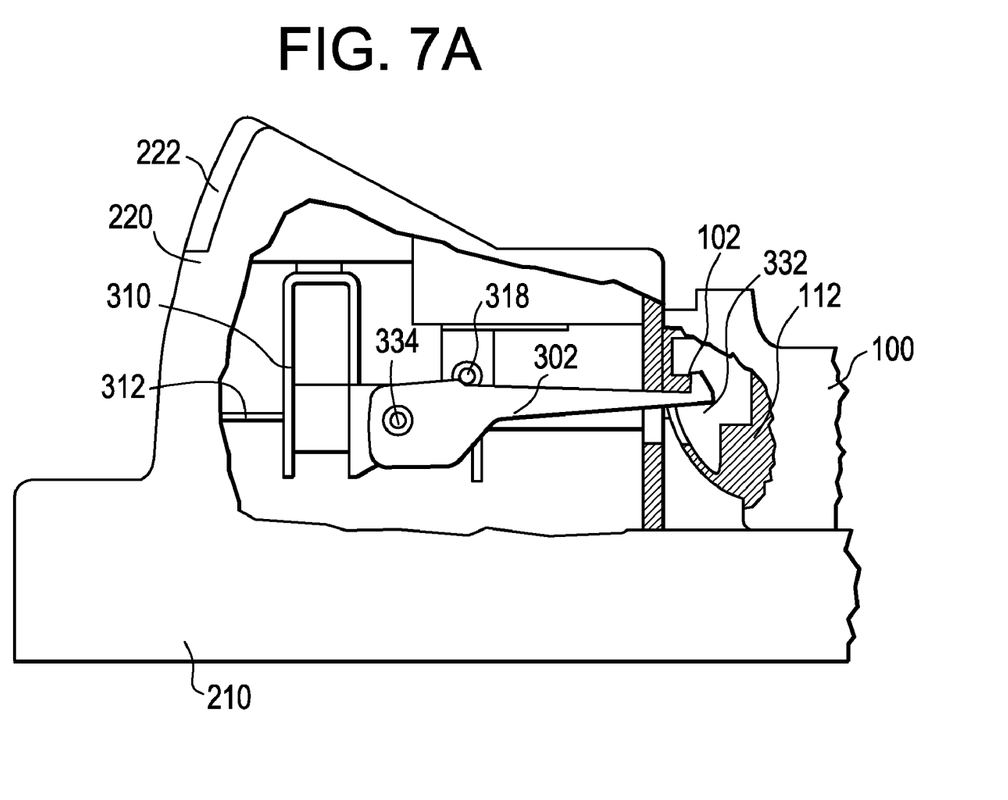

FIG. 7(a) and FIG. 7(b) show a state of connection between the top board 210 and the ultrasonic diagnosing device 100. As shown in FIG. 7(a), the hook 302 lies in its regular position and its front end is in the raised state while the low portion in the stepped portion is in contact with the pin 318. In this state, a rear surface of the ultrasonic diagnosing device 100 is in contact with the front surface of the bank 220 of the top board 210 and the branch 332 at the front end of the hook 302 is engaged with a hook receptacle 102 formed on the rear surface of the ultrasonic diagnosing device 100. The ultrasonic diagnosing device 100 has an abutting member 112 formed at a front lower position with respect to the hook receptacle 102. With the hook 302 engaged with the hook receptacle 102, the abutting member 112 does not contact the hook 302.

Figure 7B:
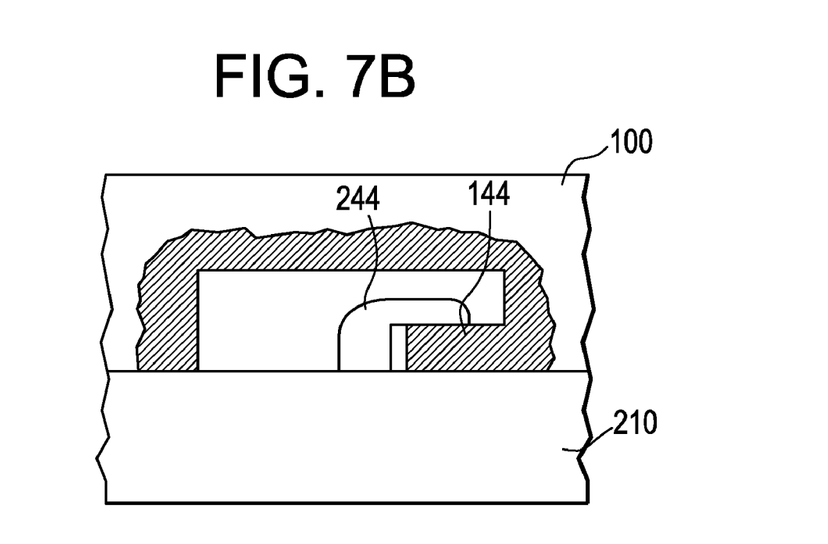

The hook receptacle 102 and the abutting member 112 are each provided two correspondingly to the two hooks 302 provided on the ceiling side. Thus, there are made connections by the hooks 302 at two positions. At this time, as shown in FIG. 7(b), the hook 244 on the flat board 240 of the top board 210 also comes into engagement with a hook receptacle 144 formed on the bottom of the ultrasonic diagnosing device 100. It follows that the ultrasonic diagnosing device 100 is connected to the top board 210 at three positions. Besides, the connector plug 402 projecting from the bank 220 is connected with the connector receptacle of the ultrasonic diagnosing device 100, whereby an electrical connection is also provided.

Figure 8:
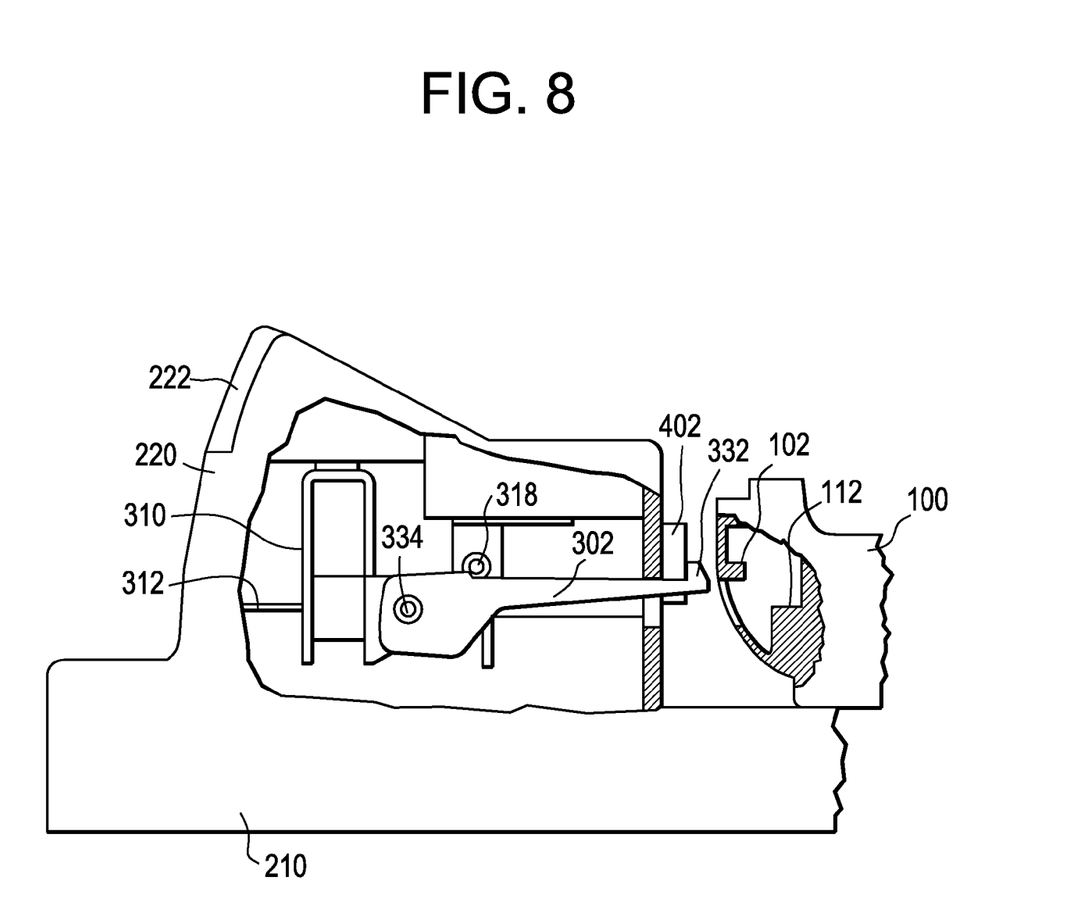
FIG. 8 illustrates a state before connection by the hook.

Such a connection is effected by pushing the rear surface of the ultrasonic diagnosing device 100 to the front surface of the bank 220. In this state, as shown in FIG. 8, first a lower edge of each hook receptacle 102 comes into contact with the inclined side face of the branch 332 of the hook 302, so that the front end of the hook 302 once lowers, then when the hook receptacle 102 passes the front end of the branch 332, the lower edge of the hook receptacle jumps up under the action of resilient force and comes into engagement with the hook receptacle 102. At the same time, the hook 244 and the hook receptacle 144 are also engaged with each other. Thus, connection of the ultrasonic diagnosing device 100 to the top board 210 can be done by simple operations.

Figure 9A:
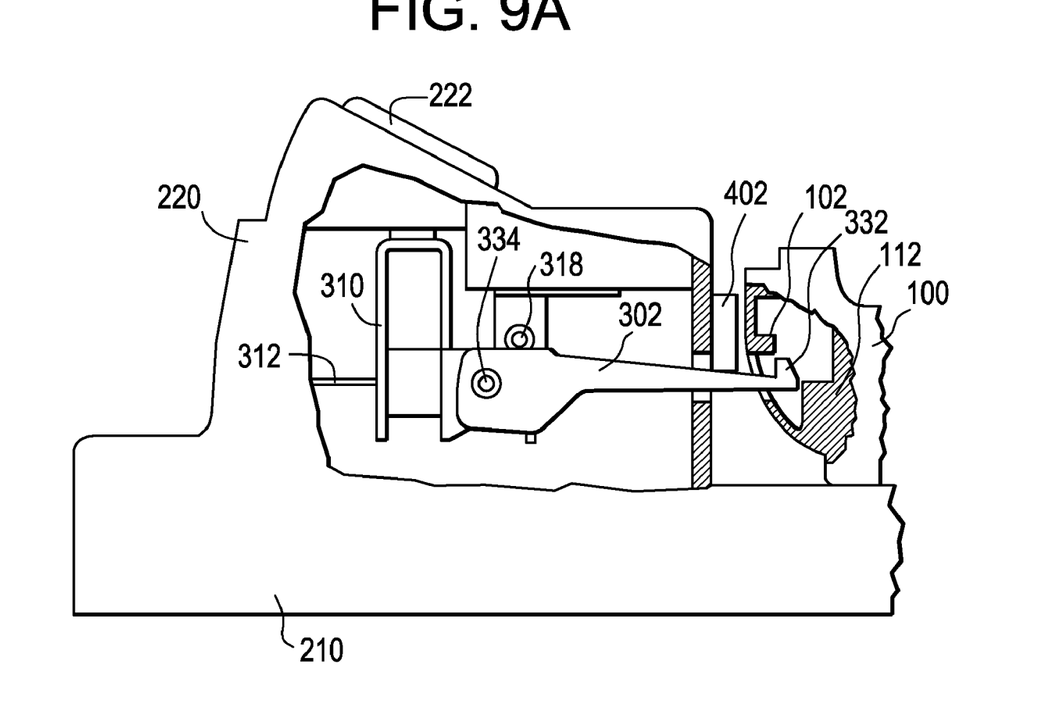

FIG. 9(a) and FIG. 9(b) show a disconnected state of the top board 210 and the ultrasonic diagnosing device 100. As shown in FIG. 9(a), when the handle 222 is pushed in forward, the hook 302 moves forward and its front end lowers while the high portion in the stepped portion is put in contact with the pin 318.

Since the amount of lowering of the front end is larger than the length of the branch 332, the hook 302 and the hook receptacle 102 become disengaged from each other.

Figure 9B:
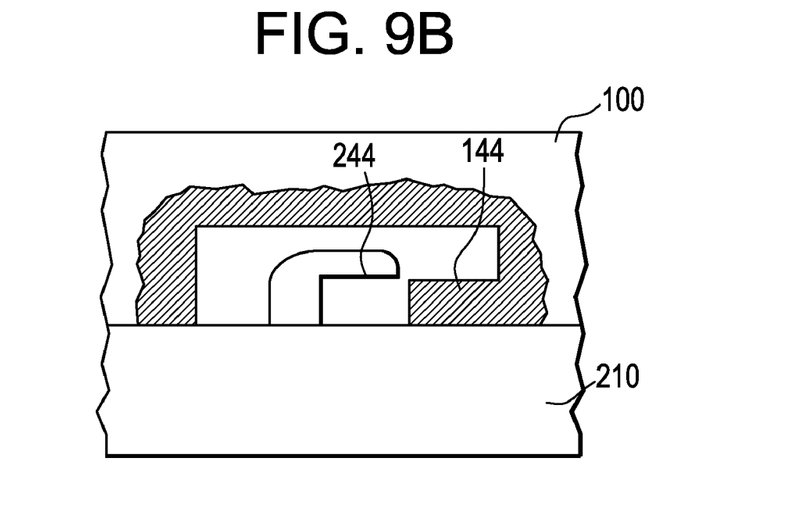

When the abutting member 112 is pushed by the front end of the hook 302 which is advancing, the ultrasonic diagnosing device 100 is pushed out forward. As a result, the rear surface of the ultrasonic diagnosing device 100 leaves the front surface of the bank 220 and the connector plug 402 is also disengaged from the connector receptacle. At this time, with displacement of the ultrasonic diagnosing device 100, the hook receptacle 144 on the bottom of the device 100 becomes disengaged from the hook 244 formed on the flat board 240 of the top board 210, as shown in FIG. 9(b). This, disconnection of the ultrasonic diagnosing device 100 and the top board 210 can also be done by simple operations.

Figure 10:
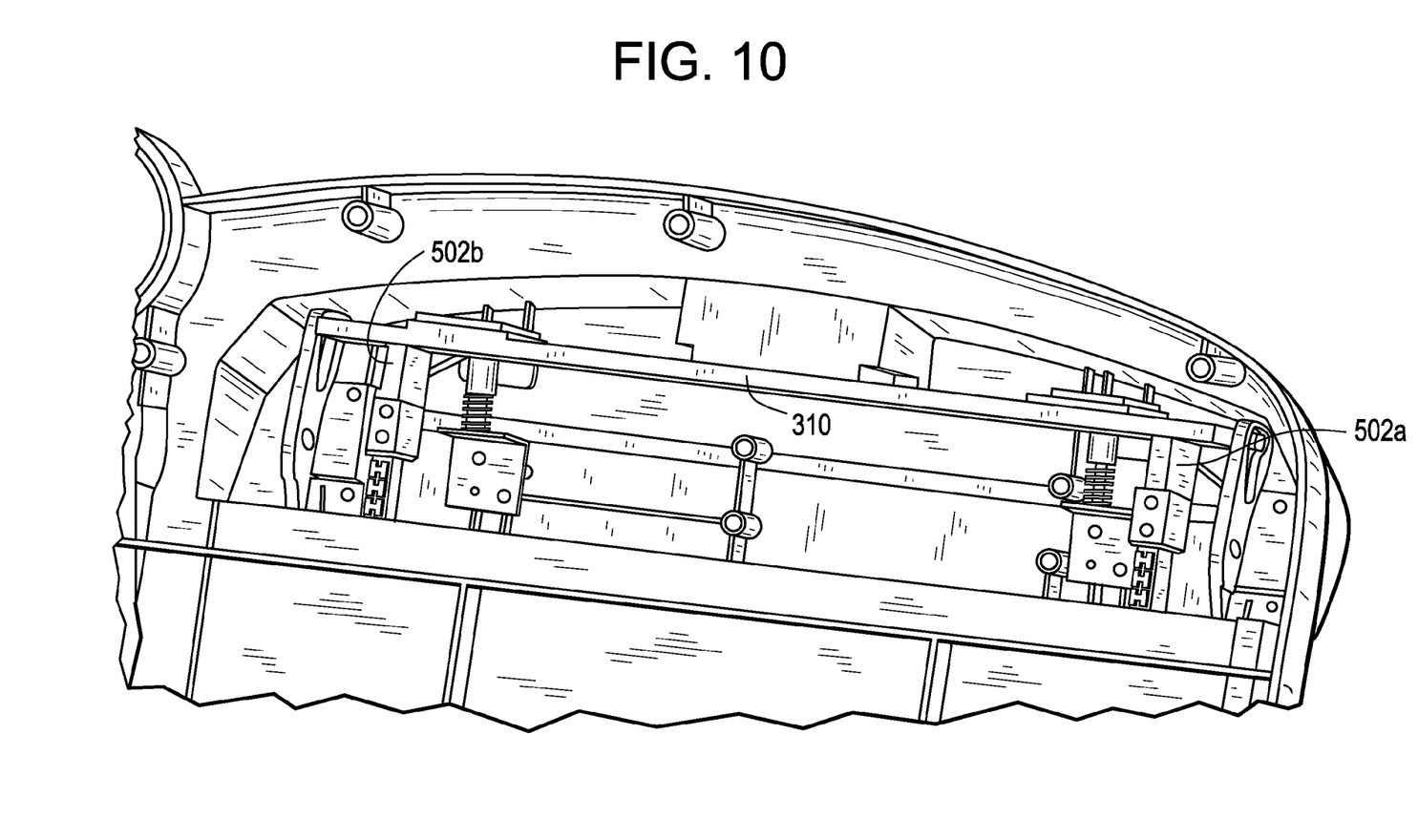
FIG. 10 illustrates the construction of another hook drive mechanism.

The bracket 310 may have a member like a beam as shown in FIG. 10, made of, for example, Aluminum die casting, instead of a press part which has a U-shaped cross section. Also, the bracket 310 may have mandrels 502a, 502b which extend in the direction of its forward movement.

Figure 11:
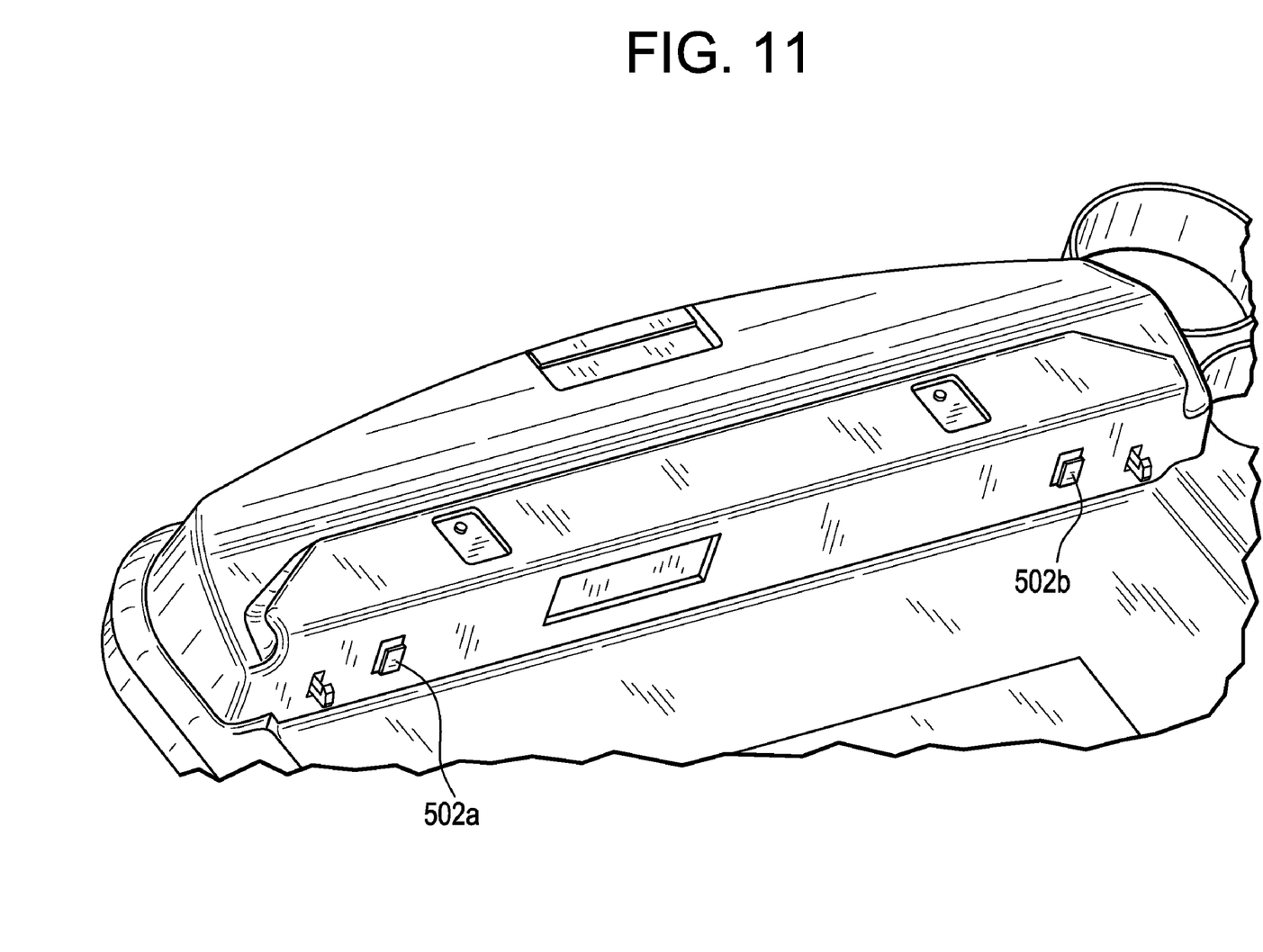
FIG. 11 illustrates placement of mandrels.

Heads of the mandrels 502a, 502b are exposed on the front wall of the bank 220 as shown in FIG. 11. When the bracket 310 moves forward, their heads project forward and eject the ultrasonic diagnosing device 100. The mandrels 502a, 502b make ejecting the ultrasonic diagnosing device 100 easier.

Many widely different embodiments of the invention may be configured without departing from the spirit and the scope of the present invention. It should be understood that the present invention is not limited to the specific embodiments described in the specification, except as defined in the appended claims.

The invention claimed is:

1. A composite apparatus comprising:
   a first unit comprising a hook portion comprising:
      a first hook including a branch extending upward at a longitudinal front end of the first hook and a camming surface, the branch including a front-end side face inclined downward toward the front end of the first hook;
   a bracket comprising a biasing member attached thereto;
      a hinge rotatably coupling the first hook to the bracket of the hook portion, the biasing member of the bracket biasing the first hook towards a rear end of the first unit; and
      a fixed pin abutting the first hook adjacent the camming surface;
      wherein the pin and the camming surface are configured to move the first hook from an upper position to a lower position when the bracket is moved in a forward direction by an external force against the bias of the biasing member and to move the first hook;
      from an upper position to a lower position when a forward external force is applied to the bracket and to move from the lower position to the upper position when the external force is removed, wherein a displacement between the upper position and the lower position is greater than a height of the branch; and
   a second unit connectable to the first unit, the second unit comprising a hook receptacle portion comprising:
      an abutting member configured to be pushed forward by the front end of the first hook to disconnect the second unit from the first unit when the first hook moves toward the lower position; and
      a first hook receptacle configured to engage the branch prior to movement of the first hook toward the lower position and to move with the abutting member to disengage from the branch when the first hook moves toward the lower position.

2. A composite apparatus according to claim 1, wherein the first unit comprises a handle coupled to the bracket and configured to apply the external force to the first hook.

3. A composite apparatus according to claim 1, wherein:
   the hook portion comprises a plurality of hooks; and
   the hook receptacle portion comprises a plurality of abutting members and a plurality of hook receptacles, each abutting member of the plurality of abutting members and each hook receptacle of the plurality of hook receptacles corresponding to a respective hook of the plurality of hooks.

4. A composite apparatus according to claim 3, wherein:
   the first unit comprises a second hook at a fixed position on the first unit; and
   the hook receptacle portion comprises a second hook receptacle configured to engage the second hook before the first hook moves toward the lower position and to move with the abutting member to disengage from the second hook when the first hook moves toward the lower position.

5. A composite apparatus according to claim 1, wherein:
   the first unit comprises an electric connector plug at a fixed location with respect to the hook portion; and
   the second unit comprises an electric connector receptacle configured to engage the electric connector plug when the first hook receptacle engages the branch of the first hook.

6. A composite apparatus according to claim 1, wherein:
   the first unit is a support base including wheels; and
   the second unit is an electronic device configured to mount on the support base.

7. A composite apparatus according to claim 6, wherein:
   the support base comprises a guide rail on an upper surface of the support base; and
   the electronic device comprises a slider on a bottom surface of the electronic device, the slider engaged with the rail when the second unit is connected to the first unit.

8. A composite apparatus according to claim 6, wherein the support base comprises an electronic circuit configured to coupled to the electronic device.

9. A composite apparatus according to claim 6, wherein the electronic device is removably coupled to the support base and is portable when removed from the support base.

10. A composite apparatus according to claim 6, wherein the electronic device is an ultrasonic diagnosing device.

11. A method of forming a composite apparatus, said method comprising:
   providing a first unit including a bracket movable in a forward direction and a backward direction with respect to the first unit wherein the bracket includes a biasing member attached thereto;
   rotatably coupling a first hook to the bracket at a hinge the biasing member configured to bias the first hook in the backward direction;
   forming a branch extending upward at a front end of the first hook, the branch including a front-end side face inclined downward toward the front end of the first hook;
   forming a camming surface on the first hook;
   coupling a pin adjacent the camming surface, the pin and the camming surface configured to move the first hook from an upper position to a lower position when a forward external force is applied to the bracket against the bias of the biasing member, wherein a displacement between the upper position and the lower position is greater than a height of the branch; and providing a second unit configured to connect to the first unit, the second unit including a first hook receptacle and an abutting member, the abutting member configured to be pushed forward by the front end of the first hook and to disconnect the second unit from the first unit when the first hook moves toward the lower position, the first hook receptacle configured to engage the branch prior to movement of the first hook toward the lower position and to move with the abutting member to disengage from the branch when the first hook moves toward the lower position.

12. A method according to claim 11, further comprising coupling a handle to the bracket, the handle configured to apply external force to the bracket.

13. A method according to claim 11, further comprising:
fixedly coupling a second hook to the first unit; and
defining a second hook receptacle in the second unit, the second hook receptacle configured to engage the second hook before the first hook moves toward the lower position and to move with the abutting member to disengage from the second hook when the first hook moves toward the lower position.

14. A method according to claim 11, further comprising:
coupling an electric connector plug to the first unit at a fixed position; and
coupling an electric connector receptacle to the second unit, the electric connector receptacle configured to engage the electric connector plug when the first hook receptacle engages the branch of the first hook.

15. A method according to claim 11, further comprising:
coupling wheels to a support base of the first unit, wherein the second unit includes an electronic device configured to be mounted on the support base.

* * * * *